(12) United States Patent
Wahrenberg et al.

(10) Patent No.: US 10,342,633 B2
(45) Date of Patent: Jul. 9, 2019

(54) MEDICAL IMAGE DATA PROCESSING SYSTEM AND METHOD

(71) Applicant: Toshiba Medical Systems Corporation, Otawara-shi (JP)

(72) Inventors: Magnus Wahrenberg, Edinburgh (GB); Tristan Lawton, Edinburgh (GB); Timothy Day, Edinburgh (GB)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 15/186,733

(22) Filed: Jun. 20, 2016

(65) Prior Publication Data

US 2017/0365051 A1    Dec. 21, 2017

(51) Int. Cl.
| | |
|---|---|
| *G06K 9/00* | (2006.01) |
| *A61B 5/05* | (2006.01) |
| *A61B 90/00* | (2016.01) |
| *G06T 15/08* | (2011.01) |
| *G06T 15/50* | (2011.01) |
| *G06T 7/70* | (2017.01) |
| *A61B 34/20* | (2016.01) |

(52) U.S. Cl.
CPC ............ *A61B 90/37* (2016.02); *G06T 7/70* (2017.01); *G06T 15/08* (2013.01); *G06T 15/50* (2013.01); *A61B 2034/2051* (2016.02); *A61B 2090/378* (2016.02); *G06T 2210/41* (2013.01)

(58) Field of Classification Search
USPC ........ 382/100, 103, 106–107, 128–134, 154, 382/162, 168, 173, 181, 219, 220, 232, 382/254, 274, 276, 286, 291, 305, 312; 600/424; 345/424, 426; 378/21, 44
See application file for complete search history.

(56) References Cited

U.S. PATENT DOCUMENTS

| | | | |
|---|---|---|---|
| 9,427,333 B2 * | 8/2016 | Satterthwaite | A61B 17/58 |
| 2009/0086894 A1 * | 4/2009 | Boyden | A61B 6/00 378/44 |
| 2014/0132605 A1 * | 5/2014 | Tsukagoshi | A61B 6/466 345/424 |
| 2014/0142426 A1 * | 5/2014 | Razzaque | A61B 18/1477 600/424 |
| 2014/0232719 A1 * | 8/2014 | Wahrenberg | G06T 15/506 345/424 |

(Continued)

OTHER PUBLICATIONS

Daniel Jönsson, et al., "A Survey of Volumetric Illumination Techniques for Interactive Volume Rendering" Computer Graphics Forum, vol. 33, Issue 1, Feb. 2014, 26 Pages.

(Continued)

*Primary Examiner* — Seyed H Azarian
(74) *Attorney, Agent, or Firm* — Oblon, McClelland, Maier & Neustadt, L.L.P.

(57) ABSTRACT

A medical image data processing system comprising processing circuitry configured to receive three-dimensional medical imaging data; and process the three-dimensional medical imaging data to generate using a virtual light source an image for display, wherein the processing circuitry is configured to vary at least one parameter relevant to the virtual light source in dependence on at least one of a position of a medical device inserted into a human or animal body, a position of a viewing point for virtual endoscopic imaging, and the progress of a procedure.

19 Claims, 7 Drawing Sheets

(56) References Cited

U.S. PATENT DOCUMENTS

2015/0022523 A1\* 1/2015 Murray ................ G06T 15/08
   345/426
2015/0164475 A1 6/2015 Kuga et al.

OTHER PUBLICATIONS

3D Guidance, Ascension Technology Corporation, 2014, 4 Pages http://www.ascension-tech.com/wpcontent/uploads/sites/15/2015/01/8300315_rev001_3DG_email_small.pdf.
Peter Shirley, et al., "A Polygonal Approximation to Direct Scalar Volume Rendering" VVS '90 Proceedings of the 1990 Workshop on Volume Visualization, 1990, pp. 63-70.

\* cited by examiner

MEDICAL IMAGE DATA PROCESSING SYSTEM AND METHOD

FIELD

The present invention relates to a medical image data processing system and method, for example a method of visualising a position of a medical device in a rendered image.

BACKGROUND

Needle guided biopsy may be used to obtain tissue samples from a patient or other subject. In needle guided biopsy, a needle is inserted into tissue and is guided using medical imaging of a region of interest. The medical imaging of the region of interest may comprise real-time imaging, for example imaging acquired using a 2D ultrasound probe. The position of the needle may be tracked using the real-time imaging. The position of the needle may alternatively or additionally be tracked using a position sensor.

A prior medical image, for example a 3D prior, may be displayed together with the real-time imaging. The 3D prior may be an image that has been acquired in advance of the needle biopsy procedure. The 3D prior may be, for example, a CT, MR or 3D ultrasound image. The 3D prior may be registered with the real-time ultrasound image.

The 3D prior may contain information that is useful to the clinician in guiding the biopsy needle. For example, the 3D prior may show the extent and location of an anatomical feature (such as a tumour) that is intended to be sampled. The 3D prior may show more information than the real-time imaging because of its 3D nature and/or because it is taken in a different modality.

In some cases, the 3D prior may be shown as a registered MPR (multi planar reformatting) image. The registered MPR image may show a slice of the 3D prior that corresponds to the planar image being shown in the real-time imaging.

In some cases, the 3D prior may be shown as a 3D volume rendered image. Displaying the 3D prior as a 3D volume rendered image may allow for an overview perspective with more context than may be obtained from an MPR image.

The 3D volume rendered image may allow the prior to be viewed from a fixed position with only the needle and probe geometry moving. A registered MPR may not give the same sense of global position and orientation as viewing the 3D prior from a fixed position with only the needle and probe geometry moving.

It is desirable to visualise the needle tip and relevant information about its surroundings. However, due to the nature of 3D volume rendering, if a representation of the needle is included in the 3D volume rendering, it may be hard to see where the tip of the needle actually is. The tip of the needle may be occluded by the surface or material into which the needle is being inserted.

Since the needle is mainly directed toward soft tissue, classical Direct Volume Rendering images of the 3D prior may look grainy. Since traditional Direct Volume Rendering may render soft tissue poorly, it may be unsuitable for rendering of the 3D prior in cases in which the main tissue type and/or the surroundings are mostly soft tissue.

Noise in the image may be made worse by local shading. The effect of the noise may be especially bad if the prior is a 3D ultrasound volume. In some circumstances, the effect of noise may make the needle geometry more difficult to see.

DESCRIPTION

Embodiments are now described by way of non-limiting example with reference to the accompanying drawings in which.

Certain embodiments provide a medical image data processing system comprising processing circuitry configured to receive three-dimensional medical imaging data; and process the three-dimensional medical imaging data to generate using a virtual light source an image for display; wherein the processing circuitry is configured to vary at least one parameter relevant to the virtual light source in dependence on at least one of a position of a medical device inserted into a human or animal body, a position of a viewing point for virtual endoscopic imaging, and the progress of the insertion procedure.

Certain embodiments provide a medical image data processing method comprising receiving three-dimensional medical imaging data; and processing the three-dimensional medical imaging data to generate using a virtual light source an image for display; wherein the processing circuitry is configured to vary at least one parameter relevant to the virtual light source in dependence on at least one of a position of a medical device inserted into a human or animal body, a position of a viewing point for virtual endoscopic imaging, and the progress of a procedure.

Figure 1:
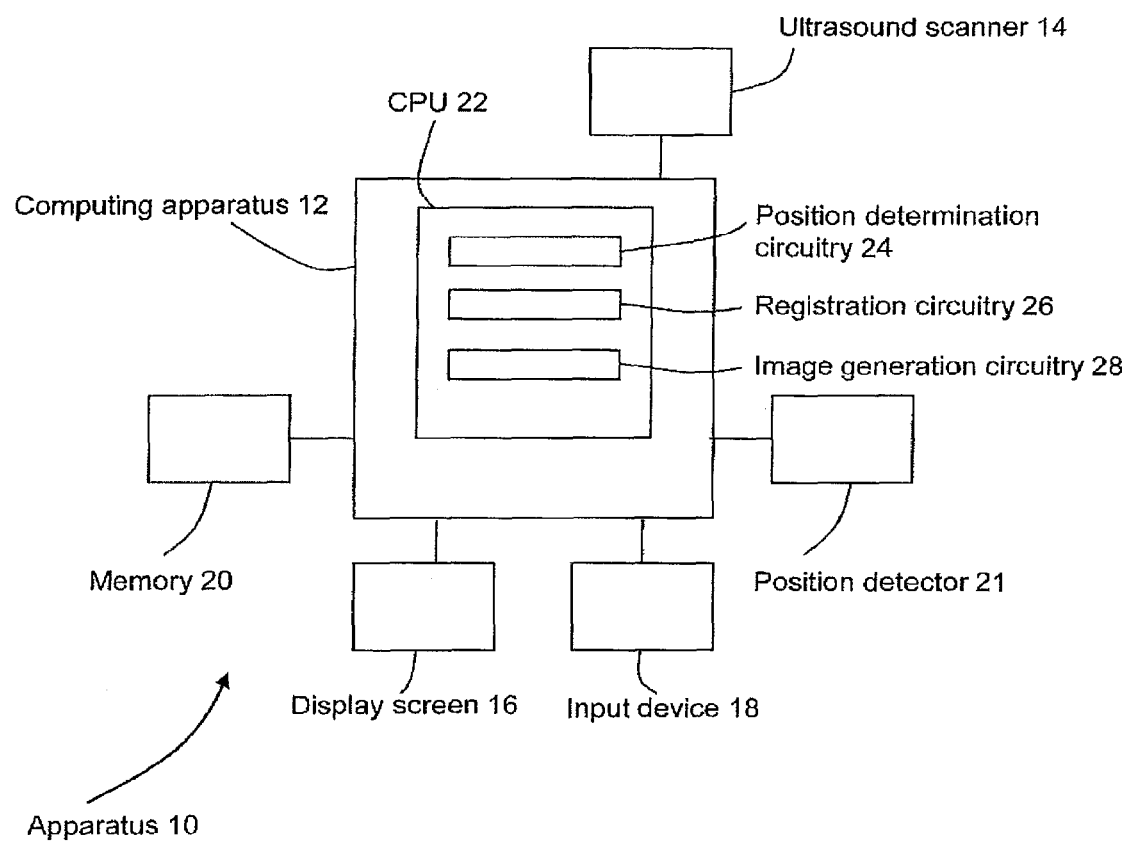
FIG. 1 is a schematic diagram of a medical image data processing system according to an embodiment.

A medical image data processing apparatus 10 according to an embodiment is shown in FIG. 1. The data processing apparatus 10 comprises a computing apparatus 12, in this case a personal computer (PC) or workstation, which is connected to an ultrasound scanner 14, one or more display screens 16 or other display device, and an input device or devices 18, such as a computer keyboard, mouse or trackball.

The ultrasound scanner 14 may be any ultrasound scanner that is configured to obtain ultrasound data representative of a region of a patient or other subject. The region of the patient or other subject may comprise at least one anatomical structure of interest.

In the present embodiment, the ultrasound scanner 14 is configured to obtain two-dimensional ultrasound data. The ultrasound scanner 14 is configured to obtain the two-dimensional ultrasound data in real-time or near-real-time. In alternative embodiments, the ultrasound scanner 14 may be replaced or supplemented by any scanner in any imaging modality that is configured to provide two- or three-dimensional medical imaging data, for example an MRI (magnetic resonance imaging) scanner, X-ray scanner, PET (positron emission tomography) scanner, SPECT (single photon emission computed tomography) scanner, or CT scanner.

The apparatus also includes a position detector 21 that is configured to determine the position of a biopsy needle that may be inserted into the body of the patient or other subject to perform a biopsy procedure. In the present embodiment, a known type of magnetic detector is used to detect the position of the biopsy needle.

In some embodiments, the position detector 21 may comprise an electromagnetic tracking system, for example a driveBAY™ or trakSTAR™ electromagnetic tracking system as produced by Ascension Technology Corporation. In some embodiments, an electromagnetic sensor is embedded into the biopsy needle (or other medical instrument). The position of the electromagnetic sensor, and therefore the position of the biopsy needle, is determined using one or more electromagnetic transmitters.

In alternative embodiments, any suitable other type of detector may be used, for example a stereo vision needle detector. A stereo vision needle detector may comprise two cameras that may track a probe and a needle and calculate their geometric relationship. In further embodiments, the position detector 21 is configured to determine the position of any suitable medical device inserted in any suitable insertion procedure.

In the present embodiment, ultrasound data sets obtained by the ultrasound scanner 14 are stored in memory 20 and subsequently provided to computing apparatus 12. In an alternative embodiment, ultrasound data sets are supplied from a remote data store (not shown) which may form part of a Picture Archiving and Communication System (PACS). The memory 20 or remote data store may comprise any suitable form of memory storage.

The memory 20 also stores three-dimensional CT data representative of the patient or other subject. The stored three-dimensional CT data has previously been obtained using a CT scanner. The stored three-dimensional CT data is used in an imaging process as described in more detail below. In an alternative embodiment, the CT data is supplied from the remote data store. In other embodiments the CT data may be replaced or supplemented by three-dimensional medical imaging data obtained using any other suitable imaging modality, for example MRI, X-ray, PET, SPECT or ultrasound imaging modalities.

Computing apparatus 12 provides a processing resource for automatically or semi-automatically processing imaging data sets, and comprises a central processing unit (CPU) 22. In the present embodiment, the computing apparatus 12 includes position determination circuitry 24, registration circuitry 26 and image generation circuitry 28.

In the present embodiment, the position determination circuitry 24, registration circuitry 26 and image generation circuitry 28 are each implemented in computing apparatus 12 by means of a computer program having computer-readable instructions that are executable to perform the method of the embodiment. For example, the position determination circuitry 24, registration circuitry 26 and image generation circuitry 28 may each be implemented as a respective computer program or algorithm that is executable by the computing apparatus 12, for example by the CPU 22. However, in other embodiments, the circuitries may be implemented, for example, as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

It is a feature of the embodiment of FIG. 1 that, as described in more detail below, during insertion of the biopsy needle into the body of the patient or other subject an Image feature representative of at least part of the biopsy needle may be displayed on an image, for example a 3D rendered image of at least part of the body of the patient or other subject, generated from the pre-obtained CT data using a rendering process. As part of the rendering process, a virtual light source may be associated with at least part of the biopsy needle such that as the needle moves the appearance of at least part of the rendered image changes. For example, a position and/or intensity of the virtual light source may change as the needle moves.

The three-dimensional rendered image generated from the CT data can, for example, be used to supplement a real-time image generated from the ultrasound data that is obtained from the ultrasound scanner 14 in real time during the insertion or withdrawal of the biopsy needle. For example, in some embodiments the image generated from the CT data may be displayed adjacent to and/or simultaneously with the ultrasound image on the display screen 16 or on different, for example adjacent, display screens, which can assist the user in determining from the images the position of the biopsy needle relative to one or more features of interest.

Figure 2:
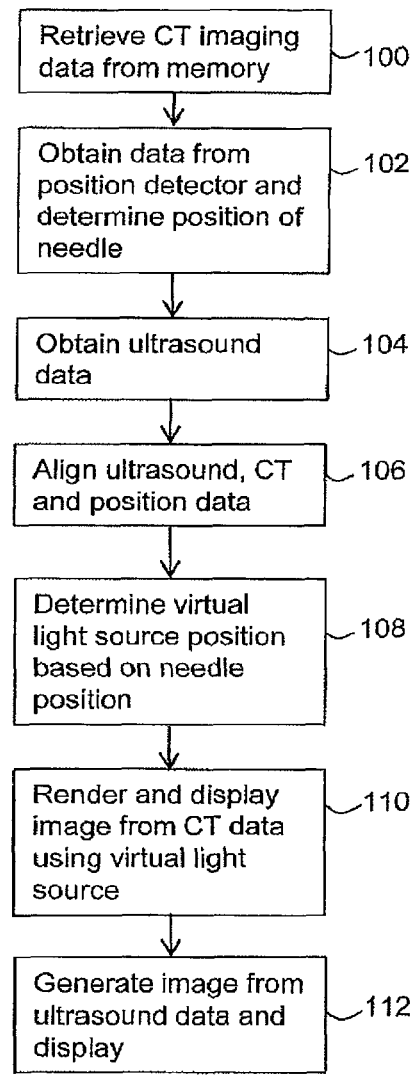
FIG. 2 is a flow chart illustrating in overview the process of an embodiment.

Operation of the system of FIG. 1 during a biopsy needle insertion procedure is illustrated in overview in the flow chart of FIG. 2.

Figure 3:
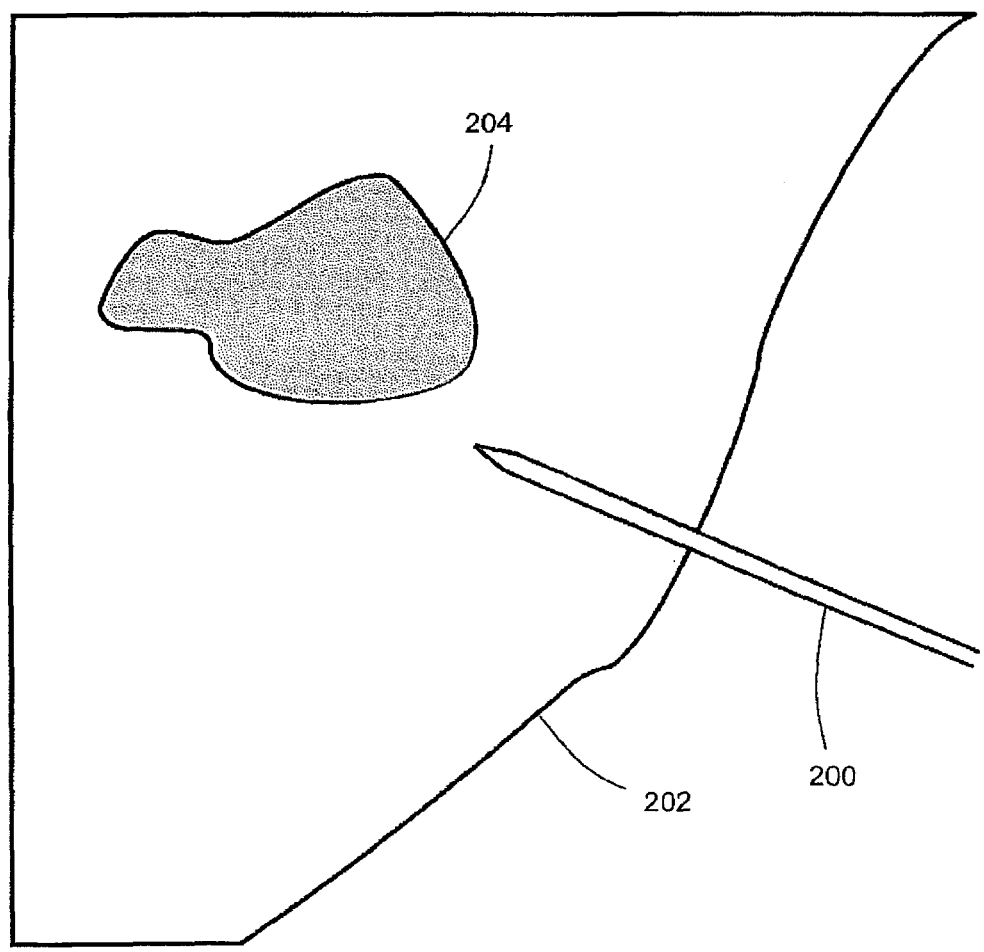
FIG. 3 is a schematic illustration of a needle biopsy image having an active virtual light source at the needle tip.

The biopsy needle insertion procedure is illustrated schematically in FIG. 3, which shows the biopsy needle 200 being inserted through the flesh 202 of the patient or other subject towards a region of interest 204 that may contain one or more points where it is desired to perform a biopsy.

At a first stage 100 of the process, the computing apparatus 12 retrieves from the memory 20 or remote data store the CT imaging data representative of the patient or other subject. In the present embodiment, the CT data comprises three-dimensional CT data comprising a set of voxels, with an intensity value of each voxel representing a level of X-ray absorption determined by a CT scan at a corresponding position within a scan volume. The CT imaging data in this embodiment is CT data that has been pre-obtained from a prior scan. In other embodiments, the computing apparatus 12 retrieves any suitable three-dimensional medical imaging data set.

At the next stage 102 of the process, the position determination circuitry 24 obtains position data from the position detector 21 representative of the position of the biopsy needle 200, and determines the current position of the biopsy needle 200 from the position data.

At the next stage 104, the computing apparatus 12 obtains real-time ultrasound data from the ultrasound scanner 14 representative of ultrasound measurements being performed using the ultrasound scanner 14 on the patient or other subject. In other embodiments, stages 100 to 104 may be performed simultaneously or in any order. In some embodiments, position data is obtained from the real-time ultrasound data rather than from a position detector 21.

Each of the CT scanner or CT data, ultrasound scanner 14 or ultrasound data, and position detector 21 or position data, may have their own co-ordinate systems such that attempts to use one or more of the ultrasound data, CT data or position data in combination with one or more of the ultrasound data, CT data or position data may result in misalignment. Therefore in the described embodiment an alignment procedure is performed to ensure that the CT data, ultrasound data and/or position data are aligned in a common co-ordinate system.

The alignment procedure is performed by registration circuitry 26, and may be based on a prior registration or calibration procedure. Any suitable registration or calibration procedure may be used. For example, an initial ultrasound data set may be obtained from the ultrasound scanner 14 and any suitable known registration procedure (for example, any suitable known rigid, affine or non-rigid registration procedure) may be used to register the ultrasound data set to the CT, thereby to obtain a translation or set of co-ordinate offsets that can be used to align the co-ordinate systems of the ultrasound data and CT data. The registration procedure may be based on, for example, intensity values in each data set and/or the position of anatomical features.

Similarly, initial position data may be obtained from the position detector 21, for instance when the biopsy needle 200 is in a known position relative to the patient or other subject (for example, touching but not penetrating the subject's skin) or in a known position relative to a patient table or the ultrasound scanner 14. The initial position data may be used by the registration circuitry 26 to determine a translation or set of co-ordinate offsets that can be used to align the co-ordinate systems of the position detector 21 or position data with one or more of the CT scanner or CT data, ultrasound scanner 14 or ultrasound data.

In the present embodiment, translations or sets of co-ordinate offsets are obtained in a prior registration or calibration procedure as described above. In stage 106 of the present embodiment, the computing apparatus 12 (for example, the registration circuitry 26) uses the translations or sets of co-ordinate offsets obtained in a prior registration or calibration procedure to align the CT data imaging data retrieved at stage 100, the position data obtained at stage 102, and the ultrasound data obtained at stage 104.

In some embodiments, the translations or sets of co-ordinate offsets may be used by the computing apparatus 16 (for example by the registration circuitry 26) to align the CT data, ultrasound data and position data, each time new CT data, ultrasound data, or position data is obtained (i.e. for each iteration of stages 100, 102 or 104) in order to align the CT data, ultrasound data and/or position data. In alternative embodiments, the translations or sets of co-ordinate offsets may be provided to one or more of the CT scanner, memory 20, ultrasound scanner 14 or position detector 21 and the alignment may be performed before the data is provided to the computing apparatus 12. In further embodiments, each of the CT data, ultrasound data and position data is generated in the same co-ordinate system and no alignment of the data is required.

After the alignment of the stage 106, the CT data is used by the image generation circuitry 28 in a rendering process to render an image of at least part of the patient or other subject. It is a feature of the embodiment of FIG. 1 that a virtual light source is used in the rendering process. Thus, at stage 108 a position of the virtual light source is determined. It is a further feature of the embodiment of FIG. 1 that the position of the virtual light source is determined at stage 108 based on the determined position of at least part of the biopsy needle 200 (as determined by the position determination circuitry 24 from the position data obtained at stage 102).

In the embodiment of FIG. 1, the virtual light source position is determined as being at a position that corresponds to the position of the tip of the biopsy needle 200. In the present embodiment, the virtual light source is a point light source.

At the next stage 110 the image generation circuitry 28 renders and displays an image by processing the CT data and using the virtual light source whose position in this embodiment is determined at stage 108 as corresponding to the position of the tip of the biopsy needle 200. Any suitable rendering method may be used, for example one of the global illumination and/or transillumination and/or photon mapping and/or ray tracing methods and/or other rendering methods, for example any method as described in US 2014/0232719, US 2015/0022523 or US 2015/0164475, the contents of each of which are hereby incorporated by reference. A rendering method used may be, for example, one of the rendering methods described in Jönsson et al, A Survey of Volumetric Illumination Techniques for Interactive Volume Rendering, Computer Graphics Forum, Volume 33, Issue 1, February 2014.

In the present embodiment, the rendering process performed by the image generation circuitry 28 comprises determining an irradiance volume by casting virtual light from each of a plurality of virtual light sources into a volume corresponding to at least part of a volume of the CT data. The volume into which the virtual light is cast includes the region of interest.

One of the virtual light sources is the virtual light source that was defined at stage 108 and is positioned at the tip of the biopsy needle 200. At least one further virtual light source is used to provide ambient illumination. In other embodiments, any number or type of virtual light sources may be used.

The irradiance due to the plurality of virtual light sources is determined at each of a large array of points in the volume using absorptive properties assigned to the voxels in dependence on voxel intensities of the CT data. The irradiance values at the array of points are stored as the irradiance volume.

In the present embodiment, a global illumination lighting model is used in the rendering process. The global illumination lighting model may include both direct illumination by light coming directly from a light source and indirect illumination, for example illumination by light that has been scattered from another surface.

The image generation circuitry 28 uses the irradiance volume to render the image for display. Rays are cast from a virtual camera (for example, one ray for each pixel of the resulting rendered image) and irradiances from points along each ray are integrated to provide pixel colours for the final rendered image.

Although in the present embodiment the rendering process is a two-pass process of determining an irradiance volume and rendering the image from the irradiance volume, in other embodiments a single-pass process may be used. Any suitable rendering technique using a virtual light source may be used. The rendering technique may or may not use a global illumination lighting model. The rendering technique may or may not include effects such as reflection, refraction and/or scattering.

In the embodiment of FIG. 1 the rendering process is a volumetric rendering process and the image displayed at stage 110 is a two-dimensional projection that may give the impression to the user of representing features in three-dimensions despite being displayed on a screen or other two-dimensional display device. The image may therefore be referred to as a three-dimensional image. The image may include, for example, one or more of shading, depth or surface texture features.

In the embodiment of FIG. 1, the image generation circuitry 28 includes in the rendered image an image feature representative of at least part of the biopsy needle 200. In this embodiment the image feature is a line overlaid by the image generation circuitry 28 on the rendered image. Any other suitable image feature may be used in alternative embodiments. In some embodiments, the image feature representative of the at least part of the biopsy needle is a polygonal geometry feature or overlaid line.

In some embodiments, no image feature representative of the needle is present in the image. Only the virtual light source represents the position of the needle.

In some embodiments, two three-dimensional images are displayed (for example, two copies of the same rendered image). One of the three-dimensional images includes a point light source, and the other of the three-dimensional images includes an image feature representative of the at least part of the biopsy needle, for example a polygonal geometry feature or overlaid line. The image feature and point light source may not be used in the same view.

At the next stage 112, the image generation circuitry 28 generates and displays a further image from the ultrasound data. Any suitable known image generation process may be used to generate the ultrasound image. For example, any suitable commercially ultrasound image processing software may be used. In the present embodiment, the image generated from the ultrasound data at stage 112 is a two-dimensional image. In other embodiments, the data received at stage 104 may be any suitable real-time data and the data received at stage 104 may be processed to obtain any appropriate two- or three-dimensional image.

Stages 102 to 112 are repeated as new data is received from the ultrasound scanner 14 and/or position detector 21. For example, the ultrasound scanner 14 may obtain several sets of ultrasound data each second. Stage 112 is repeated for each new set of ultrasound data to generate a new image. The position detector may return new position data several times per second. Stage 110 is repeated for each set of new position data.

In the present embodiment, the most recent ultrasound image is displayed on display screen 16 adjacent to the most recent rendered image. As new position data and ultrasound data are obtained, the images are refreshed.

The ultrasound image shows the ultrasound plane that is currently being imaged. The rendered image shows a three-dimensional rendered image of the region of interest, with the position of the biopsy needle 200 being indicated by the virtual light source. The position of the virtual light source in the three-dimensional rendered image changes as the biopsy needle 200 is moved.

As the virtual light source is associated with the biopsy needle 200, the appearance of the image changes as the biopsy needle 200 is inserted into, or withdrawn from, the patient or other subject. In the present embodiment, the intensity and colour of the virtual light provided by the virtual light source remain constant. However, the amount of light and the colour of light that is visible in the resulting image of stage 110 are dependent on the position of the biopsy needle 200.

If the tip of the biopsy needle 200 is close to the surface of the flesh 202, the light provided by the virtual light source at the tip of the biopsy needle 200 may appear very bright in the rendered image. If the tip of the biopsy needle 200 is inserted further into the flesh 202, the light provided by the virtual light source may appear less bright and/or redder. Furthermore, some types of tissue may absorb more light than others. Therefore, the brightness of the light in the image may be dependent on the type of tissue into which the biopsy needle 200 is inserted.

The three-dimensional rendered image supplements the two-dimensional ultrasound image. The three-dimensional rendered image may provide a fixed view of the region of interest in which the position of the biopsy needle 200 changes, while the ultrasound image provides a view that changes with the position of the ultrasound probe. The three-dimensional rendered image may allow for an overview perspective of the anatomy of interest. The three-dimensional rendered image may give a sense of global position and orientation.

The three-dimensional rendered image may provide additional anatomical information when compared with the ultrasound image. For example, the three-dimensional rendered image may be segmented to identify particular anatomical features. The three-dimensional rendered image may be a higher resolution than the ultrasound image and/or may be adapted to better detect particular features (for example, features in soft tissue).

In the present embodiment, the virtual light source is associated with the biopsy needle 200 by being positioned at the tip of the biopsy needle 200. In other embodiments, the virtual light source may be positioned relative to any suitable part of any appropriate medical device.

The use of an active light source at the needle tip may fit in well with a Global Illumination rendering model. By using Global Illumination to position a point light at the needle tip, the needle tip may be shown inside the region of interest without having to use excessive transparency or overlays.

One way of representing a biopsy needle 200 in a rendered image is to use 3D polygonal geometry. The use of a polygonal model may fit with global illumination algorithms. However, the needle geometry may be attenuated in the rendered image and may be difficult to see. Its visibility may also depend on the lighting conditions. Positioning an active light source at the needle tip may serve as an effective positional marker that may be seen more easily than inserted geometry.

If the biopsy needle 200 were represented only by a polygonal geometry, the biopsy needle 200 may be obscured when inserted into the flesh 202 unless excessive transparency were used in rendering the flesh 202. Using a high degree of transparency for rendering the flesh 202 may limit the amount of useful information that can be displayed to the user and/or make it more difficult for the user to understand representations of anatomical structures in the flesh 202.

Another way of representing the biopsy needle 200 in the rendered image is by an overlay on the rendered image. If the biopsy needle 200 is represented only by an overlay on the image, the depth of insertion of the biopsy needle 200 into the flesh 202 may not be clear to the user. The overlay may not interact with the volume in a 3D manner and may interfere with a global illumination view since it is not physical.

In some embodiments, the needle tip is represented by a virtual light source without the biopsy needle 200 also being represented by a polygonal geometry or overlay. In other embodiments, the virtual light source is used to supplement a representation of the biopsy needle 200 that uses a polygonal geometry or overlay.

In the present embodiment, the actively illuminating needle tip point may be considered to act like a beacon. The representation of the biopsy needle 200 provides its own lighting and so may not be dependent on other lighting conditions for its visibility. The representation of the biopsy needle 200 using the virtual light source interacts with the volume in a 3D manner.

The positioning of a virtual light at the tip of the biopsy needle 200 may allow the position of the tip of the biopsy needle 200 in the three-dimensional rendered image to be viewed and understood in an intuitive manner. The position of the needle tip in the two dimensions of the image is shown by the position of the light in the image. The brightness and/or colour of the light in the image may correspond to the depth of the needle tip (i.e. its position along a dimension directed into the screen) and/or the type of tissue through which the light is passing.

A proof of concept has been prepared in which a virtual light is positioned in an aneurysm. The position of the light at different positions in the aneurysm may be clearly distinguished. If the light is positioned behind the aneurysm, the brightness and quality of the light is different from images in which the light is positioned inside the aneurysm. In this case, the light acts as an effective position indicator.

In the embodiment of FIG. 1, the brightness of the virtual light emitted by the virtual light source at the needle tip remains constant (though the apparent brightness in the resulting image varies with position, for example with depth). In further embodiments, the colour and/or intensity of the virtual light emitted by the virtual light source at the needle tip is modulated to show useful volumetric properties.

Figure 4:
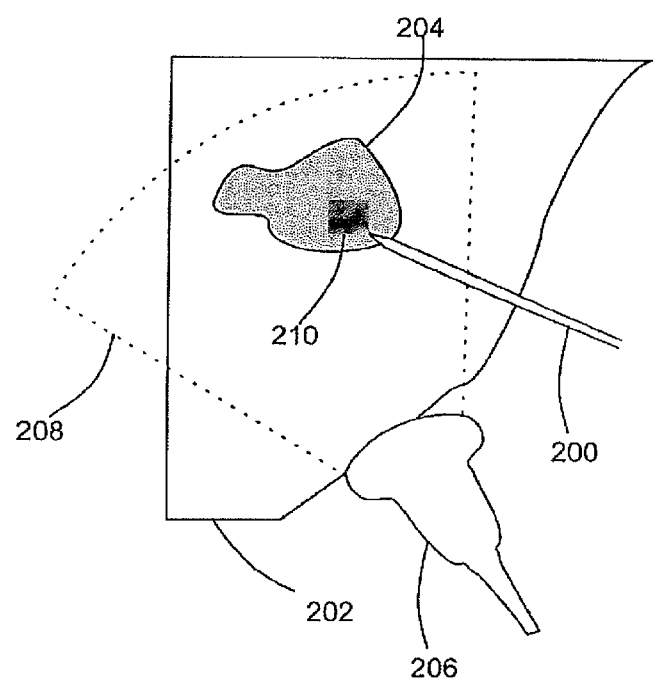
FIG. 4 is a schematic illustration showing colour and intensity modifiers based on elastography in front of the needle tip.

FIG. 4 illustrates an embodiment in which a colour of the virtual light emitted by the virtual light source at the needle tip is based on a small region of ultrasound elasticity measurement around the biopsy needle 200. Biopsy needle 200 is inserted into flesh 202 and into a region of interest 204. Ultrasound probe 206 obtains ultrasound data for an ultrasound imaging region 208 which includes region of interest 204.

Elasticity measurements are obtained for points within the region of interest. The elasticity measurements may be obtained using any suitable method and any suitable modality. For example, the elasticity measurements may be obtained from ultrasound data obtained using ultrasound probe 206. The elasticity measurements may be obtained before the insertion procedure is performed, for example before the biopsy needle 200 is inserted into the flesh. The elasticity measurements are aligned with the CT data.

For each of a set of points (for example, pixels or voxels) within the region of interest, the image generation circuitry 28 determines an elasticity value based on elasticity measurements in a small region around that point. The image generation circuitry 28 associates each elasticity value with a colour. For example, high elasticity values may be associated with red and low elasticity values with blue. The image generation circuitry 28 thereby determines a colour map for the region of interest, in which colour represents elasticity.

An inset region 210 of FIG. 4 comprises a greyscale representation of a colour map for a part of the region of interest 204. Different greyscale values are representative of different values of elasticity.

The image generation circuitry 28 determines a colour of virtual light emitted by the tip of the biopsy needle 200 using the colour map and the position of the tip of the biopsy needle 200. The colour of the virtual light emitted by the needle tip corresponds to the colour in the colour map for the position of the needle tip. For example, the position of the needle tip shown in FIG. 4 coincides with a red part of the colour map. Red virtual light is therefore emitted by the virtual light source at the needle tip when the needle tip is at this position. If the needle tip is moved into a blue part of the colour map, blue light is emitted by the virtual light source at the needle tip.

In practice, a displayed image does not display the colour map shown as the inset region 210 of FIG. 4. Instead, the virtual light emitted by the virtual light source at the needle tip changes colour as the biopsy needle 200 is moved, the colour of the virtual light source being dependent on the position of the needle tip relative to the colour map (and the colours themselves being based on elasticity measurements).

By changing the colour of the virtual light source in dependence on elasticity value, the user may be presented with an intuitive view of whether the tip of the biopsy needle 200 is in a low- or high-elasticity part of the region of interest.

Figure 5:
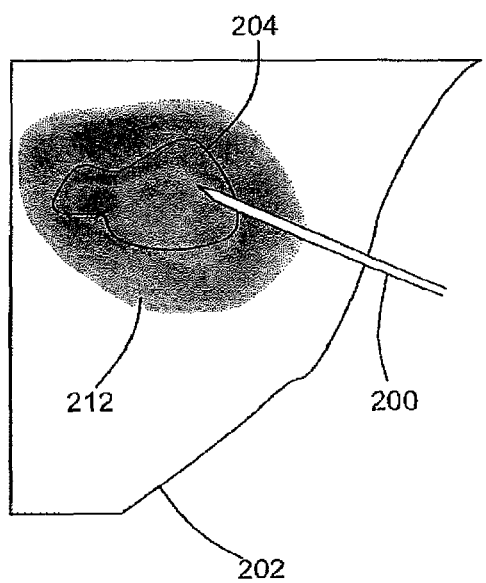
FIG. 5 is a schematic illustration showing colour and intensity modifiers based on FDG uptake from a PET/CT prior.

FIG. 5 is a schematic illustration of an embodiment in which a colour of virtual light emitted by the virtual light source associated with the needle tip is based on the measured PET FDG (Fludeoxyglucose (18F)) uptake around the needle tip. Biopsy needle 200 is inserted into flesh 202 and into region of interest 204.

FDG uptake values are obtained for points within the region of interest. In the embodiment of FIG. 5, the FDG uptake is determined from a PET/CT prior which is also used to provide the three-dimensional medical imaging data used for rendering the three-dimensional rendered image. In other embodiments, the FDG uptake may be determined from any suitable data set which may or may not be the same as the data set used in rendering the three-dimensional image. In further embodiments, a marker other than FDG may be used. Light may be modulated based on any suitable value from a nuclear medicine source, for example PET.

For each of a set of points (for example, pixels or voxels) within the region of interest, the image generation circuitry 28 determines an FDG uptake value for that point. The image generation circuitry 28 associates each FDG uptake value with a colour. The image generation circuitry 28 thereby determines a colour map for the region of interest, in which colour represents FDG uptake.

The greyscale shading 212 in FIG. 5 is representative of a colour map in which FDG uptake is represented by colours from red (high uptake) to blue (low uptake). The image generation circuitry 28 determines a colour of virtual light emitted by the tip of the biopsy needle 200 using the colour map 212 and the position of the tip of the biopsy needle 200. The colour of the virtual light emitted by the needle tip corresponds to the colour in the colour map 212 for the position of the needle tip.

In FIG. 5, the needle tip coincides with a green area of the colour map 212. Therefore, the virtual light emitted from the virtual light source at the needle tip is green. If the needle tip moves into a blue region of the colour map, the virtual light emitted by the virtual light source at the needle tip becomes blue. The colour of the virtual light at the needle tip changes with its position with regard to the colour map (and therefore with measured FDG uptake). A user can tell from the colour of the light whether the tip of the biopsy needle 200 is in a low- or high-uptake region.

In other embodiments, the colour of the light emitted by the virtual light source at the needle tip may be dependent on the value of any suitable measurement for tissue at or around the needle tip. In some embodiments, the colour of the light may be dependent on the uptake of any suitable tracer, for example any suitable tracer used for PET or SPECT imaging. The colour of the light may be dependent on the uptake of any suitable radionuclide. In some embodiments, the colour of the light is dependent on the uptake of technetium-99m. The colour of the light may be dependent on values obtained from ultrasound or MR electrography (for example, values for electrical activity), computed pressure or flow velocity from a CFD (computational fluid dynamics) simulation, or CT perfusion values.

The determination of the colour of the virtual light source may use a colour map, transfer function, or any other suitable function, or may be based directly on the measurement values without use of a colour map or transfer function.

In further embodiments, any suitable parameter of the virtual light source may be dependent on the value of any suitable measurement. For example, an intensity, colour, direction or position of the light may be dependent on a measured value (for example, a value for tracer uptake, elasticity, viscosity, pressure or flow velocity, or perfusion). A direction and/or size of a light beam or light cone produced by the virtual light source may be dependent on a measured value. In some embodiments, the virtual light source produces pulsed light and a pulse duration and/or pulse frequency of the pulsed light is dependent on a measured value.

In some embodiments, the CT data (or other three-dimensional data from which the image is rendered) is segmented before rendering. Different anatomical features may represented by different segmented regions in the CT data. A parameter of the virtual light source (for example, colour or intensity) is modulated in dependence on whether the needle tip is inside a particular segmented region.

In one embodiment, segmented regions representative of different anatomical features are associated with different colours. The user may see that the needle tip has passed into a particular segmented region by observing a change in colour of the virtual light source.

In another embodiment, a biopsy needle 200 is inserted into tissue near a liver tumour. In the rendered image, the tip of the needle 200 appears as a point light. When the needle 200 enters the tumour, the intensity of the light increases. By observing the intensity of the light, a user may see that the needle 200 has entered the tumour.

In the embodiments of FIGS. 4 and 5, a property of the virtual light source is dependent on a measurement at the needle tip position. In other embodiments, a property of the virtual light source is dependent on whether the needle tip is within a particular region, for example a segmented region. In other embodiments, a property of the virtual light source is dependent on a position of the needle tip relative to a desired position.

The desired position may be a desired collection point. A desired collection point may be a point at which it is intended to acquire a sample using the biopsy needle 200. The desired position may be defined relative to a previous collection point. For example, a desired position may be a position at a given distance from a previous collection point or points. The desired position may be defined relative to the position of a measurement. The desired position may be defined relative to a reference point. The desired position may be defined relative to a point or feature in the image or in a further image.

Figure 6:
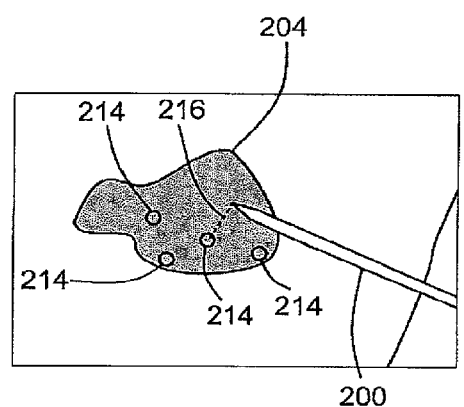
FIG. 6 is a schematic illustration showing a measurement of distance from a collection point.

FIG. 6 shows a region of interest 204 in which four desired collection points 214 have been identified. In some embodiments, the desired collection points 214 are identified using the three-dimensional rendered image. In other embodiments, the desired collection points 214 may be identified in any suitable manner.

FIG. 6 shows a distance 216 from one of the desired collection points 214 (the one nearest to the needle tip) to the tip of the biopsy needle 200. In the embodiment of FIG. 6, an intensity of the light from the virtual light source at the needle tip is dependent on the distance 216 from the needle tip to the nearest desired collection point 214. The virtual light source becomes brighter as the needle tip gets nearer to the nearest desired collection point 214 (i.e. as distance 216 decreases). In other embodiments, any suitable property of the virtual light source may change with distance 216. For example, the colour, direction, pulse duration or pulse rate of light from the virtual light source may change as the needle tip gets nearer to the desired collection point 214. In some embodiments, different desired collection points 214 may be associated with different colours of light.

In the embodiment of FIG. 6, the Intensity of the light is dependent on the distance from the needle tip to a desired collection point 214. In other embodiments, a property of the light is dependent on whether the needle tip is near a location that has previously been biopsied (a previous collection point). Any suitable property of the light may be based on the distance to previous collection points 214 and/or a distance to pre-planned collection points 214.

In some embodiments, a property of the light is based on a distance from an anatomical feature. For example, a property of the light may be based on a distance from a segmented region such as a region representative of a tumour. A property of the light may be based on a distance from an anatomical landmark.

In some embodiments, a property of the light is based on a distance from a further device, for example from a further needle. In one embodiment, multiple needles are inserted into a patient for cryogenic ablation. A respective virtual light source is associated with each of the needles. A colour and/or intensity of each virtual light source is based on a spacing between that needle and a neighbouring needle.

In some embodiments, a property of the light is based on a distance from a position that is associated with a further image. For example, in some embodiments a reference position is determined from a further image. A property of the light is based on the distance between the needle tip and the reference position. The further image may be the ultrasound image generated at stage 112, or may be a different image. In some embodiments, a reference plane is determined from a further image, and a property of the light is based on the distance between the needle tip and the reference plane.

Figure 7:
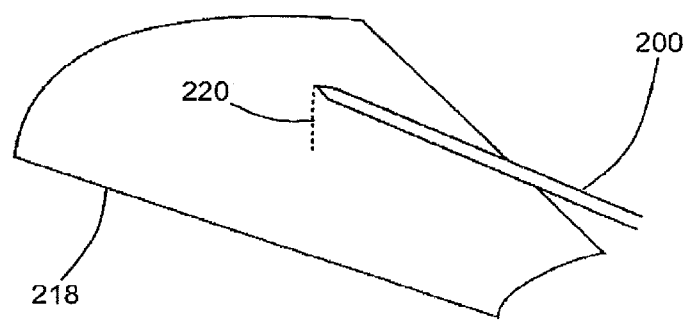
FIG. 7 is a schematic illustration showing a measurement of distance from a live ultrasound plane.

FIG. 7 illustrates a further embodiment in which a colour and/or intensity of the virtual light source at a needle tip is dependent on an offset of the needle tip from a live 2D ultrasound plane 218 corresponding to the ultrasound image obtained by ultrasound scanner 14. In FIG. 7, the tip of the biopsy needle 200 is offset from the live 2D ultrasound plane 218 by a distance 220. Therefore the current ultrasound view (as shown on the ultrasound image generated at stage 112 of FIG. 2) is out of alignment with the needle 200. In the embodiment of FIG. 7, the intensity of the virtual light source becomes brighter when the needle 200 is aligned with the live 2D ultrasound plane. In other embodiments, any suitable parameter of the virtual light source is based on the distance from the live ultrasound plane (which may be described as a misalignment measurement).

In the embodiments described above with reference to FIGS. 1 to 7, the position data is representative of the position of the needle 200, and the virtual light source is positioned at the tip of the needle 200. In other embodiments, the virtual light source may be positioned relative to any part of the needle 200. In some embodiments, a distributed virtual light source or plurality of light sources is placed along the length of the needle 200. Therefore, the user views the whole needle 200 as producing light, rather than just the tip. In some embodiments, the tip of the needle 200 produces a greater amount of virtual light than other points along the needle 200.

In the embodiments of FIG. 1 to 7, the virtual light source positioned at the tip of the needle is a point light source. In other embodiments, the virtual light source is a directional light source. In one embodiment, the virtual light source at the tip of the needle emits a beam or cone of light towards the nearest desired collection point. The beam or cone of light acts as an indicator of which direction to move the needle in. In other embodiments, the beam or cone of light may be aligned with an axis of the needle 200. The beam or cone of light may be aligned with a direction of travel of the needle 200.

In the embodiments of FIGS. 1 to 7, the position data acquired by the position detector 21 is representative of the position of the biopsy needle 200, and the virtual light source is associated with the biopsy needle 200. In other embodiments, the position data may be representative of the position of any medical device that is inserted into a human or animal body. The virtual light source may be associated with any suitable part of the medical device. The virtual light source may be placed at a tip of the medical device. The virtual light source may be distributed along at least part of a length of the medical device.

The image generation circuitry 28 may be configured to vary any parameter of the virtual light source in accordance with a position of any part (for example, any point or region) of the medical device.

The virtual light source may be associated with a part of the medical device that is configured to perform a medical device process. The medical device process may comprise, for example, taking a biopsy sample or performing an ablation. The medical device process may comprise acquiring an image. The part of the medical device that is configured to perform the medical device process may comprise, for example, a camera, a point, a blade or an antenna. The medical device may be inserted for the performance of a insertion procedure (for example, a biopsy needle insertion procedure) that comprises one or more medical device processes (for example, one or more biopsies). Each medical device process may be performed at a respective position.

The medical device may be, for example, a needle, a stent, a replacement body part, a prosthetic, a measurement device, a surgical device, a valve, a heart valve, an imaging device, an endoscopic device, a catheter, an implant, or an electronic device. The electronic device may be, for example, an endoscope or an ultrasonic probe. The insertion procedure may comprise, for example, a biopsy needle insertion procedure, an endoscopy, a catheterization, an implant insertion procedure. The virtual light source may be a point light source or a distributed light source.

In some embodiments the medical device is an endoscope. The virtual light source may be associated with a point on the endoscope, for example with the tip of the endoscope. The virtual light source may be positioned at a viewing point of the endoscope. An image may be rendered in which a property of the virtual light source is dependent on the position of the viewing point of the endoscope.

In some embodiments, the medical device is a catheter and the virtual light source is associated with a tip of the catheter. In some embodiments, the medical device is an implant and the virtual light source is associated with a point on the implant, for example a corner, centre point, reference point or attachment point.

In one embodiment, the medical device is an ultrasound probe configured to perform transesophageal echocardiography (TOE or TEE). A virtual light source is associated with the ultrasound probe.

In embodiments, any parameter of the virtual light source may be varied in dependence on the progress of a procedure. For example, any parameter of the virtual light source may be varied in dependence on progress of an insertion procedure. A parameter of the virtual light source may be varied in dependence on a duration of the insertion procedure. For example, the colour and/or intensity of the virtual light source may change with time. A parameter of the virtual light source may change in dependence on a stage of the insertion procedure than has been reached, for example a number of medical device processes that have been performed. For example, a colour of the virtual light source may change in dependence on the proportion of desired samples that have been collected. A parameter of the virtual light source may change with a level of completeness of the insertion procedure.

In the embodiments described above, one or more parameters of a virtual light source are varied. In other embodiments, the image generation circuitry 28 is configured to vary at least one parameter relevant to the virtual light source, which may or may not be a parameter of the virtual light source itself. For example, the image generation circuitry 28 may vary a colour or other property of any part of the image, for example a part of the image representative of an anatomical feature, or of the whole image. The image generation circuitry 28 may be configured to vary any parameter of the image generation process.

In some embodiments, a virtual light source may be used that is not positioned on the medical device. For example, a virtual light source may be placed at a desired position such as a desired collection point. Parameters of the virtual light source at the desired position may be varied in dependence on a distance of the medical device from the desired position. For example, the virtual light source at the desired position may change in colour and/or intensity as the medical device approaches the desired position. In some embodiments, the parameters of the virtual light source that is not positioned on the medical device may be varied in dependence on the progress of the insertion procedure. For example, a colour of the image may be changed when a medical device process has been successfully performed.

In some circumstances, using a virtual light source positioned on the medical device may provide an Image that it easier to interpret than an image in which the virtual light source is not positioned on the medical device. For example, it may be easy to see how a point light source moves in relation to its surroundings, while it may be relatively difficult to see how a small object like the needle moves in relation to the point light source.

In some embodiments, the three-dimensional rendered image is a virtual endoscopic image and a virtual light source is positioned at, or relative to, a viewing point of the virtual endoscopic image. In some embodiments, a virtual endoscopic image is rendered in addition to the three-dimensional rendered image.

A virtual endoscopic image may comprise, for example, a virtual view that is generated from a point of view of an endoscope, so as to simulate an image that would be delivered by a camera positioned on an endoscope during an endoscopy. Alternatively or additionally the image may comprise a representation of the endoscope itself.

In some embodiments, a position of a viewing point of a virtual endoscopic image (for example, a position from which the viewer appears to be viewing the image) may correspond to a position of a tip of an endoscope. In some embodiments, the image generation circuitry 28 is configured to vary at least one parameter relevant to the virtual light source (for example, at least one colour or intensity) in dependence on a position of the viewing point of the virtual endoscopic image. For example, the colour or intensity of the virtual light source may vary as the viewing point approaches a point or region of interest.

In some embodiments, the computing apparatus 12 is configured to receive user input and to use the user input in the processing of the three-dimensional medical image data. In some embodiments, the image generation circuitry 28 is configured to receive user input and to position the virtual light source relative to the medical device based on the user input. For example, the user may instruct the image generation circuitry 28 to place a virtual light source on the tip of the medical device, or at any suitable position of the medical device. The user may select parameters of the virtual light source. The user may select which parameters of the virtual light source will vary in dependence on the position of the medical device. For example, the user may select whether they wish the virtual light source to change in colour and/or intensity as the medical device approaches a desired position.

The user may select a region of interest and/or anatomical feature to be displayed in the image. The user may select a representation of the medical device. For example, the user may select whether to represent the medical device using one or more of an overlay, a polygonal geometry and a virtual light source. The user may switch on or off any of the possible representations.

Certain embodiments may provide a medical imaging apparatus comprising a medical imaging device, a tracked biopsy needle and display apparatus; in which a light source is used to visualize the needle tip location in a prior scan as a point light.

The colour and/or intensity of the light may be modulated based on a measurement of elasticity around the needle using ultrasound elastography. The colour and/or intensity of the light may be modulated based on a value from a nuclear medicine source, for example PET. The colour and/or intensity of the light may be modulated based on the needle's distance to points from which biopsy samples have already been gathered. The colour and/or intensity of the light may be modulated based on the needle's distance to pre-planned biopsy points. The colour and/or intensity of the light may be modulated based on the needle's height above a live ultrasound plane.

A beam or cone of light may also be cast towards the nearest point as an indicator of which direction to move the needle in.

While many embodiments have been described with regard to a needle, any medical device may be used. The medical device may be inserted into any part of any human or animal body. A virtual light source may be placed at, or relative to, any suitable location on any medical device. The virtual light source may indicate the position of the medical device in a three-dimensional image of at least part of the body of a human or animal subject, when the medical device is inserted into the body of that human or animal subject. The medical device may be used in any suitable medical or veterinary procedure.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the Invention. The accompanying claims and their equivalents are intended to cover such forms and modifications as would fall within the scope of the invention.

The invention claimed is:

1. A medical image data processing system, comprising: processing circuitry configured to
receive three-dimensional medical imaging data representative of a region of a human or animal body and of at least part of a medical device inserted into the human or the animal body;
and
process the three-dimensional medical imaging data to generate, using a viewpoint positioned on the human's or the animal body's surface side with respect to the medical device and a virtual light source positioned away from the viewpoint, an image for display, wherein the processing of the three-dimensional medical imaging data to generate the image for display comprises (1) positioning the virtual light source in a virtual space of the three-dimensional imaging data such that the virtual light source is positioned in the virtual space of the three-dimensional imaging data at or near a representation of at least part of the medical device, or (2) positioning the virtual light source in the virtual space of the three-dimensional imaging data such that the virtual light source is positioned in the virtual space of the three-dimensional imaging data at or near a representation of a desired position to which the medical device is to be moved,
wherein the processing circuitry is further configured to vary at least one parameter relevant to the virtual light source in dependence on at least one of a position of the medical device inserted into the human or the animal body and progress of a procedure,
wherein the positioning of the virtual light source relative to the representation of the at least part of the medical device by the processing circuitry comprises at least one of positioning the virtual light source at or near a tip of the medical device;
positioning the virtual light source at or near a part of the medical device configured to perform a medical device process; and
distributing the virtual light source along at least part of a length of the medical device.

2. The system according to claim 1, wherein the processing of the data to generate the image by the processing circuitry comprises associating the virtual light source with at least part of the medical device.

3. The system according to claim 2, wherein the associating of the virtual light source with at least part of the medical device by the processing circuitry comprises positioning the virtual light source relative to the representation of the at least part of the medical device.

4. The system according to claim 1, wherein the virtual light source comprises at least one of a point light source and a distributed light source.

5. The system according to claim 1, wherein the processing circuitry is further configured to receive user input and process the three-dimensional medical imaging data based on the user input.

6. The system according to claim 1, wherein the progress of the procedure comprises at least one of a duration of the procedure, a level of completeness of the procedure, and a number of medical device processes performed.

7. The system according to claim 1, wherein the procedure comprises movement of the medical device to a desired position, and the processing circuitry is further configured to vary the at least one parameter in dependence on a position of the medical device relative to the desired position.

8. The system according to claim 7, wherein the desired position comprises at least one of
a desired position relative to a selected anatomical feature,
a desired position relative to a position of a measurement,
a desired position relative to a position associated with a further image, and
a desired position relative to an ultrasound plane.

9. The system according to claim 7, wherein the desired position comprises a desired position relative to at least one of
a position where it is desired for the medical device to perform a medical device process,
at least one prior position where at least one medical device process has previously been performed,
a desired biopsy position, and
at least one previous biopsy position.

10. The system according to claim 1, wherein the processing circuitry is further configured to receive further data representative of at least one property of the human or the animal body, and the varying of the at least one parameter comprises varying of the at least one parameter in dependence on the at least one property of the human or the animal body.

11. The system according to claim 10, wherein said further data comprises a result of a measurement.

12. The system according to claim 11, wherein the measurement comprises at least one of an ultrasound measurement, an electrography measurement, a PET measurement, a SPECT measurement, a CT measurement, a CT perfusion measurement, an elasticity measurement, and a viscosity measurement.

13. The system according to claim 10, wherein the at least one property of the human or the animal body comprises at least one of elasticity, viscosity, uptake of a radionuclide, uptake of a radioactive tracer, FDG (Fludeoxyglucose (18F)) uptake, technetium-99m uptake, electrical activity, computed pressure, computed flow, and CT perfusion.

14. The system according to claim 1, wherein the at least one parameter that is varied by the processing circuitry comprises at least one property of the virtual light source.

15. The system according to claim 14, wherein the at least one property of the virtual light source comprises at least one of:
intensity of the virtual light source,
colour of the virtual light source,
direction of the virtual light source,
position of the virtual light source,
at least one of direction and size of a light beam or light cone produced by the virtual light source, and
at least one of pulse duration or pulse frequency of light produced by the virtual light source, wherein the virtual light source produces pulsed light.

16. The system according to claim 1, wherein the at least one parameter varied by the processing circuitry comprises at least one parameter of a global illumination process.

17. The system according to claim 1, further comprising at least one display device, wherein the processing circuitry is further configured to display on the at least one display device the image adjacent to or overlaid with a further image.

18. The system according to claim 1, wherein the medical device comprises at least one of a needle, a stent, a replacement body part, a prosthetic, a measurement device, a surgical device, a valve, an imaging device, an endoscopic device, a catheter, an electronic device, an implant, and an ultrasound probe.

19. A medical image data processing method, comprising:
receiving three-dimensional medical imaging data representative of a region of a human or animal body and of at least part of a medical device inserted into the human or the animal body; and
processing the three-dimensional medical imaging data to generate, using a viewpoint positioned on the human's or the animal body's surface side with respect to the medical device and a virtual light source positioned away from the viewpoint, an image for display, wherein the processing of the three-dimensional medical imaging data to generate the image for display comprises (1) positioning the virtual light source in a virtual space of the three-dimensional imaging data such that the virtual light source is positioned in the virtual space of the three-dimensional imaging data at or near a representation of at least part of the medical device, or (2) positioning the virtual light source in the virtual space of the three-dimensional imaging data such that the virtual light source is positioned in the virtual space of the three-dimensional imaging data at or near a representation of a desired position to which the medical device is to be moved,
wherein the method further includes varying at least one parameter relevant to the virtual light source in dependence on at least one of the position of a medical device inserted into the human or the animal body and progress of a procedure,
wherein the positioning of the virtual light source relative to the representation of the at least part of the medical device comprises at least one of positioning the virtual light source at or near a tip of the medical device;
positioning the virtual light source at or near a part of the medical device configured to perform a medical device process; and
distributing the virtual light source along at least part of a length of the medical device.

* * * * *